United States Patent [19]

Tennican et al.

[11] Patent Number: 5,411,485
[45] Date of Patent: May 2, 1995

[54] CATHETER ACCESS SYSTEM AND METHOD

[75] Inventors: Patrick O. Tennican; L. Myles Phipps; Russell A. Michaelsen, all of Spokane, Wash.

[73] Assignee: Hyprotek, Spokane, Wash.

[21] Appl. No.: 187,632

[22] Filed: Jan. 26, 1994

Related U.S. Application Data

[63] Continuation-in-part of Ser. No. 48,906, Apr. 19, 1993, Pat. No. 5,308,322.

[51] Int. Cl.⁶ .............................................. A61M 5/00
[52] U.S. Cl. .................................... 604/191; 604/181; 128/655
[58] Field of Search ...................... 604/83, 87, 88, 183, 604/185, 191, 30, 36, 38, 62, 64, 89, 91, 173, 187, 188, 218, 232, 240, 258

[56] References Cited

U.S. PATENT DOCUMENTS

| | | |
|---|---|---|
| Re. 29,207 | 5/1977 | Bolduc et al. . |
| 1,740,174 | 12/1929 | Hevern . |
| 1,948,388 | 2/1934 | Liberson . |
| 2,168,686 | 8/1939 | Saffir . |
| 2,254,994 | 9/1941 | Butland . |
| 2,711,740 | 6/1955 | Pickens . |
| 2,812,765 | 11/1957 | Tofflemire . |
| 3,467,096 | 9/1969 | Horn ................................ 604/191 |
| 3,528,404 | 9/1970 | Chan . |
| 3,572,336 | 3/1971 | Hershberg ........................ 604/173 |
| 3,714,943 | 2/1973 | Yanof et al. ..................... 604/191 |
| 3,863,624 | 2/1975 | Gram ................................ 604/191 |
| 3,941,126 | 3/1976 | Dietrich et al. . |
| 3,957,082 | 5/1976 | Fuson et al. . |
| 4,109,653 | 8/1978 | Kozam et al. . |
| 4,121,739 | 10/1978 | Devaney et al. . |
| 4,191,183 | 3/1980 | Mendelson . |
| 4,257,416 | 3/1981 | Prager . |
| 4,367,737 | 1/1983 | Kozam et al. . |
| 4,471,765 | 9/1984 | Strauss et al. ................... 604/181 |
| 4,512,764 | 4/1985 | Wunsch . |
| 4,601,666 | 9/1986 | Pizzino . |
| 4,609,371 | 9/1986 | Pizzino . |
| 4,666,429 | 5/1987 | Stone . |
| 4,689,047 | 8/1987 | Bauer . |
| 4,758,235 | 7/1988 | Tu . |
| 4,784,157 | 11/1988 | Halls et al. . |
| 4,795,441 | 1/1989 | Bhatt . |
| 4,915,688 | 4/1990 | Bischof et al. . |
| 4,915,695 | 4/1990 | Koobs . |
| 5,037,390 | 8/1991 | Raines et al. . |
| 5,147,323 | 9/1992 | Haber et al. . |

FOREIGN PATENT DOCUMENTS

737249 6/1966 Canada .
WO92/11044 7/1992 WIPO .

*Primary Examiner*—C. Fred Rosenbaum
*Assistant Examiner*—Perry E. Van Over
*Attorney, Agent, or Firm*—Wells, St. John, Roberts, Gregory & Matkin

[57] ABSTRACT

A catheter access system includes a syringe body having at least two barrels. The syringe body includes an axle integrally formed thereof. Such also includes an independent fluid conduit associated with each of the two barrels. The fluid conduits extending toward a base end of the syringe body at spaced locations. An independent plunger is associated with each of the two barrels. An associated valve body has a bore provided therethrough, with the syringe body axle being received in such bore to support the valve body and syringe body relative to one another for rotation about the syringe body longitudinal axis. The valve body has a first fluid passageway positioned to align with either selected one of the syringe body fluid conduits when the valve body and syringe body are selectively rotated relative to one another. A second fluid passageway isolated from the first fluid passageway is provided in the valve body to enable air or other fluid to be discharged separately relative to the catheter. A retaining cap is provided at the outer base end of the axle. The retaining cap has a radial extent which is greater than the diameter of the axle, and bears against the valve body to rotatably retain the valve body and unitary body together in fluid tight communication. Longitudinal rotation of the valve body in space is restricted relative to the syringe body and patient, such that rotational movement is imparted to the syringe body to access a given barrel.

46 Claims, 8 Drawing Sheets

CATHETER ACCESS SYSTEM AND METHOD

This patent resulted from a continuation-in-part patent application of U.S. patent application Ser. No. 08/048,906, filed Apr. 19, 1993, which became U.S. Pat. No. 5,308,322, and which is entitled "Central Venous Catheter Access System And Syringes".

TECHNICAL FIELD

This invention relates to methods of and systems for accessing catheters which are invasively inserted relative to a patient's blood stream, and to the maintenance of such catheters.

BACKGROUND OF THE INVENTION

Catheters are commonly used to provide quick and direct access to a patient's blood stream. Such range from a basic intravenous line in a patient's arm to more critical-care central venous catheters (CVC). Catheter maintenance can be costly and troublesome, especially for all but the simplest short term catheters which merely continuously drip fluid into a patient's arm vein.

For example, a CVC is inserted by a surgical procedure and extends to a location very near the heart. A CVC is often left in place for a relatively long time. The skin entry point is kept covered by a carefully monitored dressing. Because of the direct nature of access to the blood stream, infection control when dealing with CVCs is of utmost importance. In most institutions, only registered nurses and doctors are allowed to perform procedures relating to CVC access.

CVCs include an external access lumen having a terminus injection/withdrawal port which typically includes a Luer-lok connector. One form of an injection port which is mated with the connector is a pierceable rubber membrane. Fluid transfer through such a port requires first cleaning the pierceable membrane with alcohol and/or Betadine, and then inserting a hypodermic syringe needle through the membrane to provide direct access to the blood stream. Alternately, such an injection port can be removed enabling a syringe tip having an appropriate luer-lok connector to be directly connected to the catheter access lumen.

CVC access lumens can become clogged by clotted blood. The access lumens are kept free from clots when not in use by injecting a heparin solution into them, which is commonly referred to as a heparin lock. Heparin is a protein material which acts as a blood anticoagulant to interfere with blood clotting. Before withdrawing a blood sample from a CVC, the heparin and the blood containing heparin which is in the catheter is first withdrawn. Also depending on the patient's condition and type of catheter, it is sometimes desirable or necessary to withdraw heparin from the catheter before injecting a medication through the catheter.

There are significant risks associated with transferring fluid through a CVC. One risk is that of microbial infection. Another significant risk is that of air embolism. Both of these risks are potentially life-threatening and increase significantly with each access through the CVC access lumen, especially when such an access is by way of a needle and pierceable membrane. Compounding these risks is the fact that a single medication injection procedure or a single blood collection procedure can require four or more separate connections to the CVC access lumen, one for each separate fluid injection and withdrawal. In some cases, the CVC is used for medication injection or blood withdrawal as many as four to six times each day. Thus, as many as twenty-four CVC connections are required every day, with a corresponding number of opportunities for infection or air embolism. Over the period of a month, the CVC could present over 700 opportunities for life-threatening events to occur.

As an example, a simple medication injection procedure requiring heparin withdrawal includes the following steps. First, the pierceable membrane of the injection port must be cleaned with alcohol. The success of this step is highly dependent on the skill of the care-giver and is subject to mistakes caused by carelessness or inattentiveness. A needle of a waste blood withdrawal syringe is then inserted through the membrane. The syringe is operated to withdraw the heparin-containing blood from the CVC. Then, the treatment protocol requires a saline syringe to be utilized to flush the catheter. A medication syringe is then prepared, its needle inserted through the pierceable membrane, and medication injected into the CVC. Subsequently, another saline flush syringe is prepared and utilized to carry all the medication into the patient's blood stream. Finally, a syringe containing heparin is injected into the CVC through the pierceable membrane to re-establish the heparin lock. If all this is done quickly and correctly, the catheter should not clot, no air embolism should result, and the patient shouldn't get an infection.

Withdrawing or collecting blood requires similar steps. First, all heparin-containing blood is withdrawn from the CVC transfer lumen by injecting a needle through the pierceable membrane and withdrawing blood into a syringe. The needle of a waste blood withdrawal syringe is then inserted through the membrane, and the syringe is operated to withdraw heparin-containing blood from the CVC. After the heparin-containing blood is completely withdrawn from the catheter, the waste withdrawal needle is removed and a needle of another syringe is inserted to withdraw non-heparin contaminated blood. Then a normal saline flush of 20 milliliters is injected, followed by another heparin flush with yet another needle and syringe.

As is apparent from the above discussion, another problem with standard CVC access procedures is that the various solutions and syringes needed to access a CVC are supplied separately. Often, a nurse must track down each piece of equipment separately. This can be a costly and time consuming process. Furthermore, even after proper equipment is found, such equipment is often not designed to work together as a system.

In part because of this, CVC procedures are performed only by registered nurses or doctors, with the procedure consuming a large quantity of their valuable time. The patient and other care-giver personnel are often forced to remain idle while waiting for the qualified persons to find time to provide the catheter access service.

As an additional complication, access to a CVC by needle gives rise to a potential source of injury and infection to the care-giver through contact with the needle. This is particularly important when the patient being treated has a dangerous infection, such as HIV or hepatitis. Often, the care-giver and patient are unaware that an infection is present.

In addition to CVC maintenance and operation as described above, it can be highly desirable in emergency situations to get a plurality of medications quickly into a patient's bloodstream through a CVC or other catheter. It would be highly desirable in such situations for the care-giver to have a catheter access system which facilitates multiple accesses to the catheter.

Our U.S. Pat. No. 5,308,322, formerly U.S. patent application Ser. No. 08/048,906, is hereby incorporated by reference.

BRIEF DESCRIPTION OF THE DRAWINGS

Preferred embodiments of the invention are described below with reference to the following accompanying drawings.

FIG. 13 is a sectional view of the FIG. 11 system taken through line 13—13 of FIG. 12.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In accordance with one aspect of the invention, a catheter access system comprises:

a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;

an independent plunger associated with each of the two barrels;

a valve body operatively connected in fluid tight communication relative to the syringe body base end, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient; and a non-invasive restriction means externally associated with the valve body to engage between the valve body and the patient for restricting longitudinal rotational movement of the valve body in space relative to the syringe body and patient when so engaged, said external restriction means enabling substantial free rotational movement of the syringe body in space relative to the valve body and the patient when so engaged.

In accordance with another aspect of the invention, a catheter access system comprises:

a unitary syringe body having a base end, an outer end, a longitudinal axis and at least two longitudinally extending barrels; the unitary syringe body including an axle integrally formed of the unitary syringe body; the axle having an outer base end, having a diameter and extending outwardly of the syringe body base end along the syringe body longitudinal axis; the unitary syringe body including an independent fluid conduit associated with each of the two barrels, the two independent fluid conduits extending from their respective barrels toward the syringe body base end at spaced locations;

an independent plunger associated with each of the two barrels;

a valve body having a bore provided therethrough, the syringe body axle being received through the valve body bore to support the valve body and unitary syringe body relative to one another for rotation about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient; and a retaining cap provided at the outer base end of the unitary syringe body axle, the retaining cap having a radial extent which is greater than the diameter of the axle, the retaining cap bearing against the valve body to rotatably retain the valve body and unitary body together in fluid tight communication.

In accordance with a further aspect of the invention, a catheter access system comprises:

a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;

an independent plunger associated with each of the two barrels;

a valve body operatively connected in fluid tight communication relative to the syringe body base end, the valve body and syringe body being mounted for rotation relative to one another about the syringe body longitudinal axis;

the valve body including a first fluid passageway positioned to align with either selected one of the syringe body fluid conduits when the valve body and syringe body are selectively rotated relative to one another, the valve body including a first outlet comprising a needle-less mating connector in fluid communication with the first fluid passageway for connection with a catheter access line in a patient; and the valve body including a second fluid passageway isolated from fluid communication with the first fluid passageway, the second fluid passageway being positioned to align with either selected one of the syringe body fluid conduits when the valve body and syringe body are selectively rotated relative to one another, the valve body including a second outlet in fluid communication with the second fluid passageway.

In yet still a further aspect of the invention, a catheter access system comprises:

a syringe body having a base end, an outer end, a longitudinal axis and at least two longitudinally extending first and second barrels, the syringe body including a first fluid conduit associated with the first barrel and extending toward the syringe body base end, the syringe body including a separate second fluid conduit associated with the second barrel and extending toward the second body base end, an independent plunger associated with each of the first and second barrels; and the syringe body including an externally accessible longitudinally extending cavity sized to receive a separate longitudinally elongated fluid container, the syringe body including a third fluid conduit, the third fluid conduit extending from the cavity toward the syringe body base end.

More particularly and first with reference to FIGS. 1–7, a preferred embodiment catheter access system is indicated generally with reference numeral 10. Such principally comprises a unitary syringe body 12, a valve body 14, and a substantially rigid supporting sheet 16. Valve body 14 and syringe body 12 are operatively connected in fluid-tight communication, with valve body 14 being supported relative to rigid sheet 16. A lumen and Luer-lok connector 18 extends from valve body 14 for connection with a catheter access line 20 which has previously been implanted into a patient.

Figure 1:
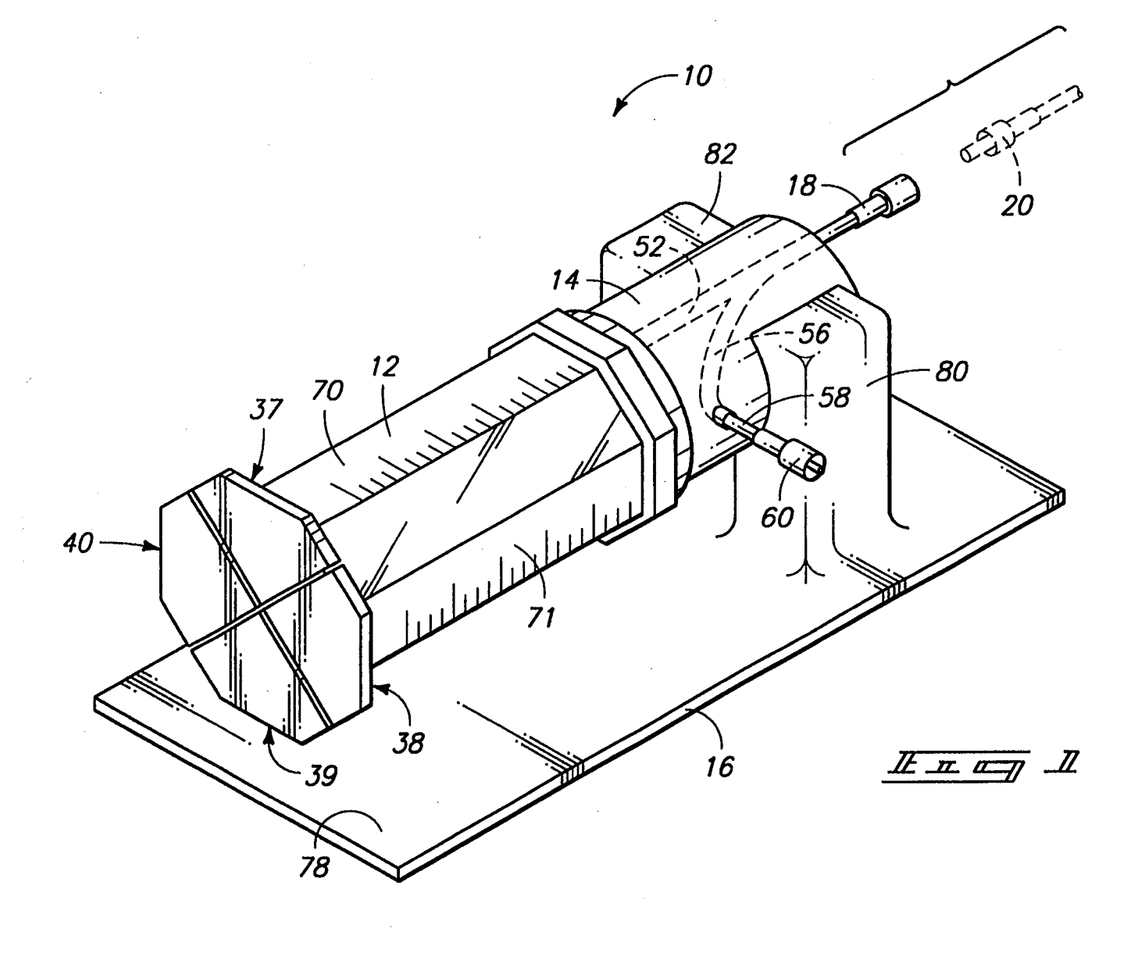
FIG. 1 is an isometric view of a catheter access system in accordance with the invention.
Figure 2:
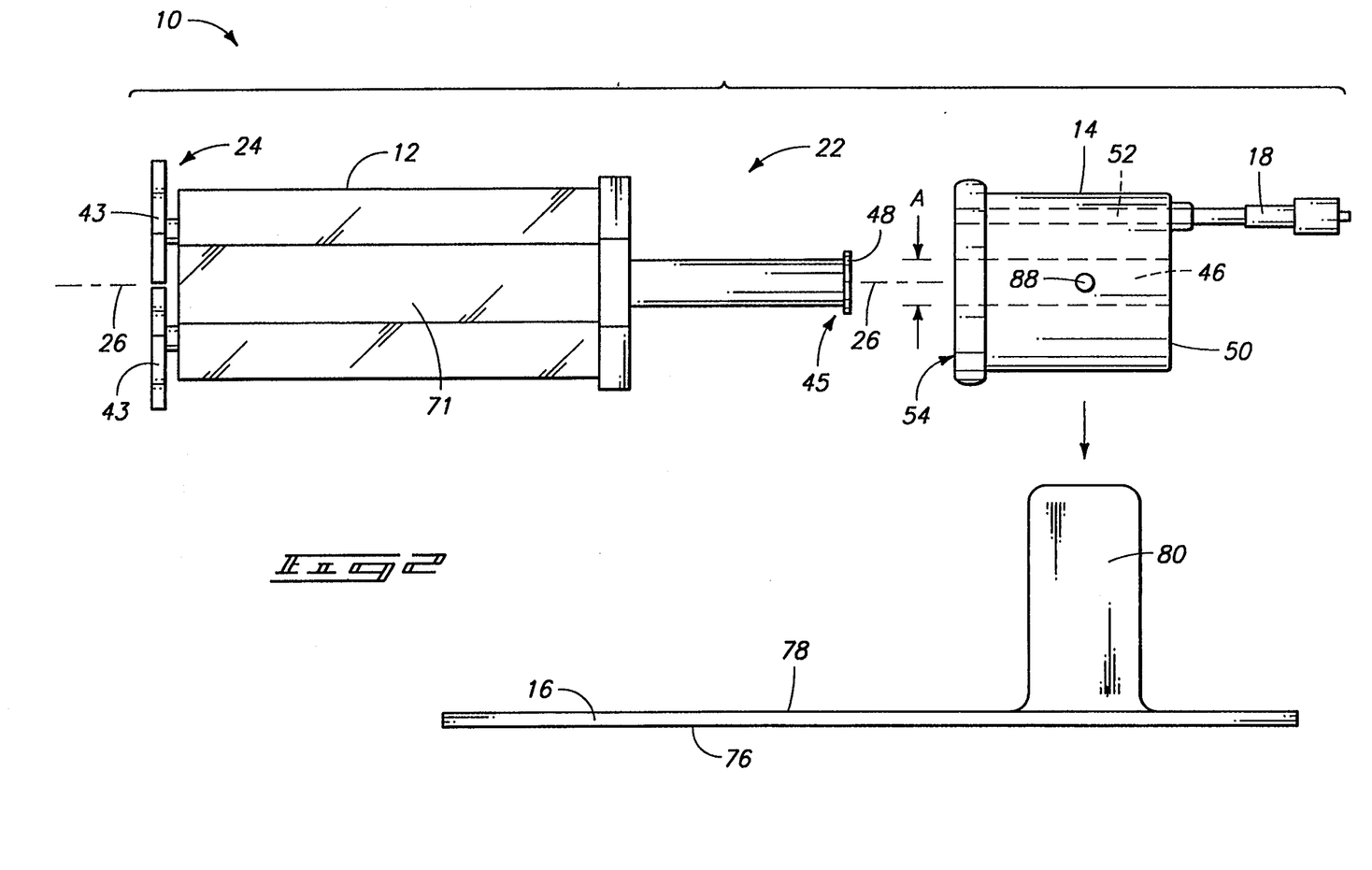
FIG. 2 is a side, partially exploded, view of the catheter access system of FIG. 1.
Figure 3:
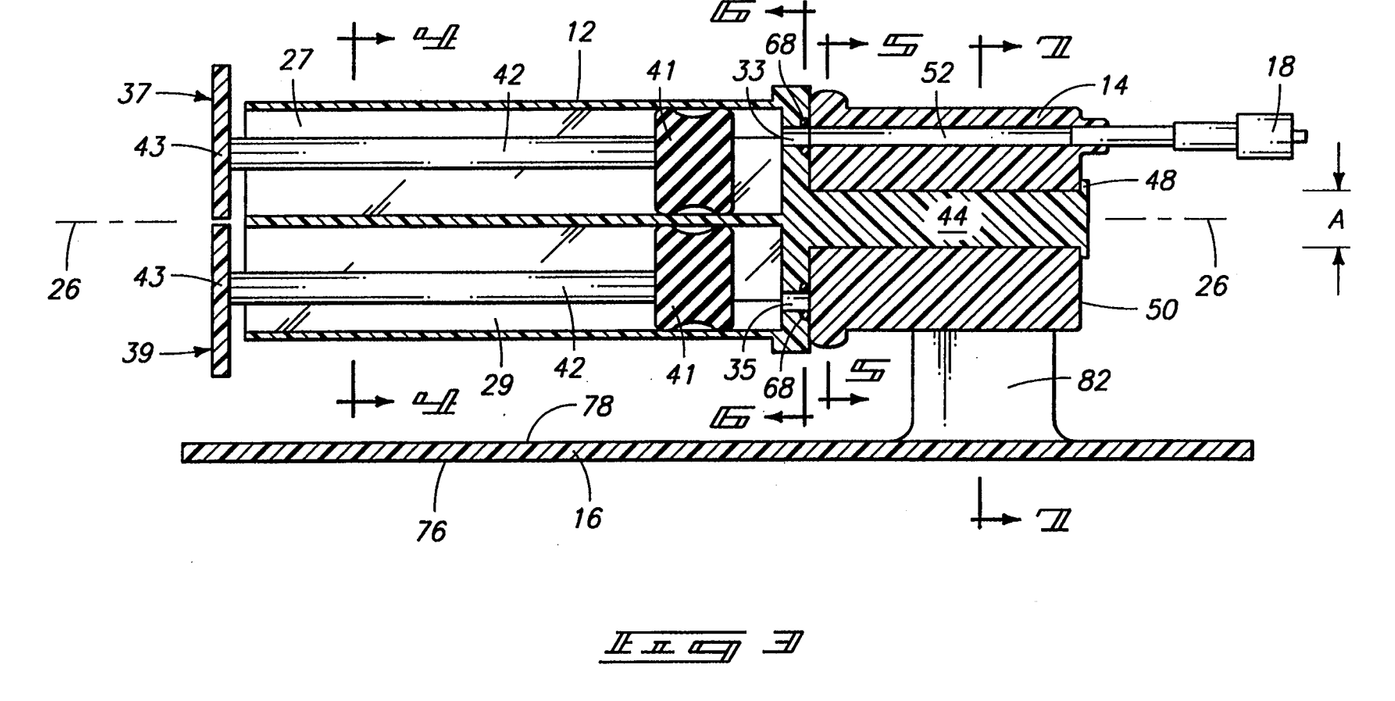
FIG. 3 is a central longitudinal sectional view of the FIG. 1 system.
Figure 4:
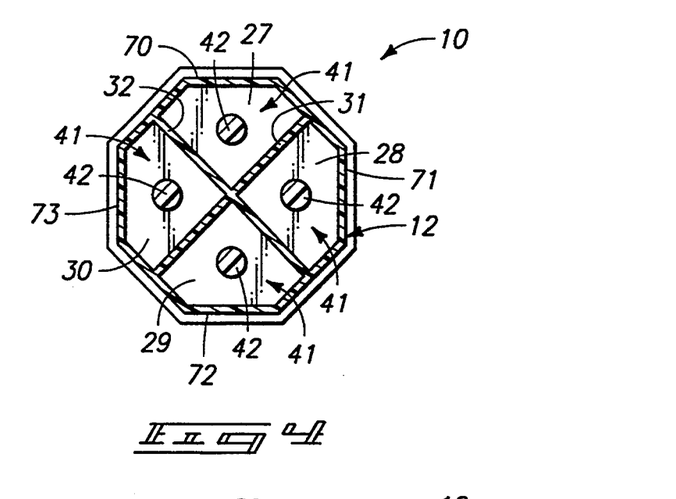
FIG. 4 is a sectional view of the FIG. 1 system taken through line 4—4 of FIG. 3.
Figure 5:
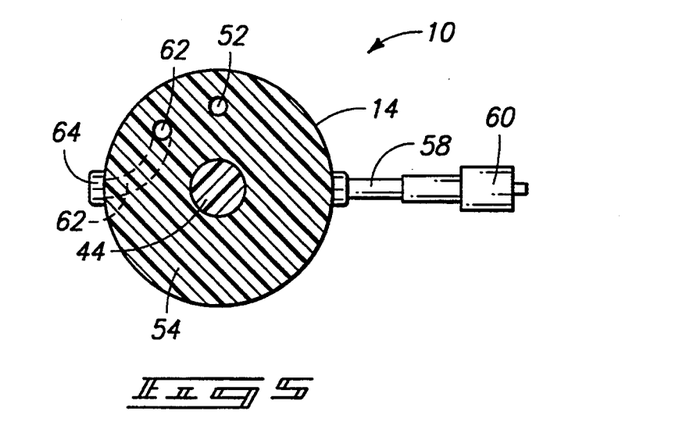
FIG. 5 is a sectional view of the FIG. 1 system taken through line 5—5 of FIG. 3.
Figure 6:
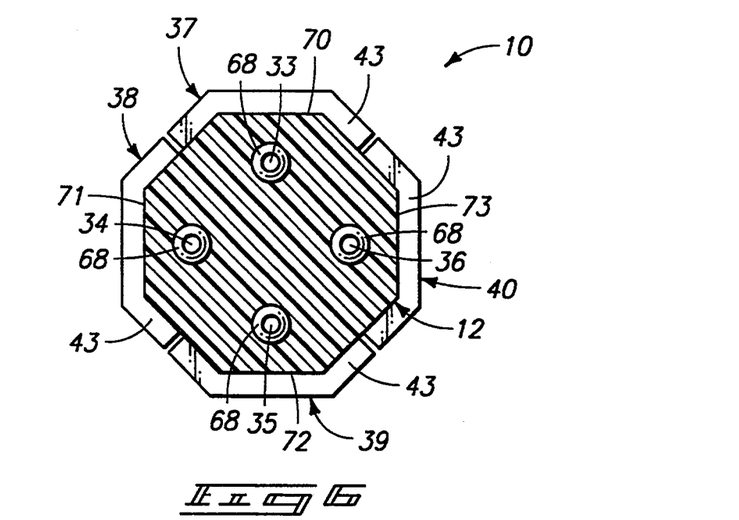
FIG. 6 is a sectional view of the FIG. 1 system taken through line 6—6 of FIG. 3.
Figure 7:
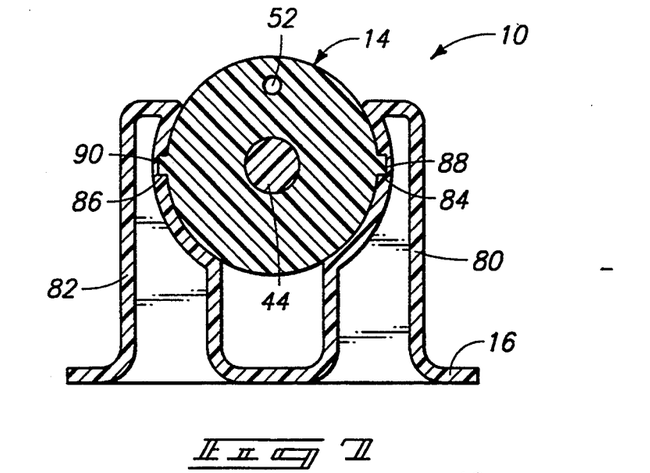
FIG. 7 is a sectional view of the FIG. 1 system taken along line 7—7 of FIG. 3.

More specifically, syringe body 12 is provided as a substantially unitary body having a base end 22, an outer end 24, and a longitudinal axis 26. Syringe body 12 is octagonal in cross-sectional shape, with axis 26 being centrally positioned relative to the mass of syringe body 12. Other shapes and arrangements are of course contemplated, with the invention being limited only by the accompanying claims. Four longitudinally extending barrels 27, 28, 29 and 30 are provided internally within syringe body 12. Such are defined and separated by a pair of perpendicularly intersecting walls 31 and 32. In accordance with the invention, at least two longitudinally extending barrels are provided in connection with a syringe body to provide a multi-barreled catheter access system. Independent fluid conduits are associated at least with each of such two barrels in a multi-barreled syringe. In the illustrated and preferred embodiment, independent fluid conduits 33, 34, 35 and 36 are associated with barrels 27, 28, 29 and 30 respectively, and extend from their respective barrels towards syringe body base end 26 at spaced locations relative to one another. Plunger assemblies 37, 38, 39 and 40 are associated with syringe barrels 27, 28, 29 and 30, respectively. Each includes a pentagonal-shaped stopper 41, a longitudinally extending rod 42, and a pentagonal-shaped thumb/access button 43.

Syringe body 12 includes an axle 44 integrally formed thereof. Axle body 44 extends outwardly of syringe body base end 22 along syringe body longitudinal axis 26, and includes its own respective outer base end 45. Axle 44 has a diameter "A" (FIG. 2). Valve body 14 is provided with a bore 46 (FIG. 2) through which syringe body axle 44 is received for rotatably supporting syringe body 12 and valve body 14 relative to one another for rotation about syringe body longitudinal axis 26.

A retainer cap 48 is provided at outer base end 45 of syringe body axle 44. Such has a radial extent which is greater than diameter "A" of axle 44, and bears against valve body 14 to rotatably retain valve body 14 and syringe body 12 together in fluid-tight communication. More specifically, valve body 14 includes an outermost base end surface 50 against which retainer cap 48 directly bears for longitudinally pulling syringe body 12 and valve body 14 tightly against one another. Thus, retainer cap 48 directly contacts against valve body 14 in the illustrated embodiment. Retainer cap 48 can be provided as an integrally formed part of syringe body 12 and axle 44. In such instance, valve body 14 would be manufactured in at least two pieces for fitting and subsequent interconnection about axle 44 and relative to cap 48. Alternately, retainer cap 48 could be a separate component from axle 44. In such instance, valve body 14 can be manufactured essentially as a single component, with retainer cap 48 being welded or otherwise attached after valve body 14 is slid onto axle 44.

Referring more specifically to valve body 14, such includes an inner end 54 (FIG. 2) opposite base end surface 50. A first fluid passageway 52 extends between inner end 54 and base end surface 50, and is positioned to align with any selected one of syringe body fluid conduits 33, 34, 35 or 36 when valve body 14 and syringe body 12 are selectively rotated relative to one another. An outlet for passageway 52 is provided in the form of a needle-less mating Luer-lok connector 18 for connection with catheter access line 20 in a patient.

Valve body 14 further comprises a transfer lumen or passageway 56 (FIG. 1) extending or branching from first fluid passageway 52 to a location external of valve body 514. Such is shown in the illustrated embodiment to include an external tube 58 which extends to a Luer-lok connector 60 for engagement with a separate syringe for transferring fluid between the patient catheter 20 and separate syringe through valve body first fluid passageway 52 and transfer lumen 56. Alternate connections, such as a membrane pierceable by a needle of the syringe, would also of course be usable.

Valve body 14 further includes a second fluid passageway 62 (FIG. 5) which is isolated from fluid communication with first fluid passageway 52. Second fluid passageway 62 is positioned to align with any selected one syringe body fluid conduit 33, 34, 35 or 36 when valve body 14 and syringe body 12 are selectively rotated relative to one another. Second fluid passageway 62 extends to a one-way check valve 64 which allows fluid to flow out, but not in. The valve body base end internal opening of second fluid passageway 62 is rotationally oriented 45° relative to the position of the valve body internal end opening of first fluid passageway 52.

Syringe body conduits 33, 34, 35 and 36 are positioned at 90° rotational angles relative to one another. Such relative positioning enables only any one of the syringe body fluid contents to be aligned in fluid communication with either of first fluid passageway entrance 62 or second fluid passageway entrance 52 at any given point in time. First fluid passageway 52 provides access to a patient's catheter. Second fluid passageway 62 provides selective independent access to any one of syringe barrels 27, 28, 29 and 30 apart from patient catheter access at a given point in time. Such might be useful, for example, in removing an air bubble from within any one of the syringe barrels prior to pushing medication therefrom into the patient through first fluid passageway 52.

Suitable means are preferably provided for assuring a fluid-tight seal between valve body 14 and syringe body 12. In the illustrated embodiment, such is preferably provided in the form of four O-rings 68 which are received within corresponding axial grooves about each conduit 33, 34, 35 and 36 at base end 26 of syringe body 12. Such tightly bear against flat inner end surface 54 (FIGS. 3 and 5) to prevent leakage of fluid from any syringe barrel when its associated fluid conduit is not aligned with valve body fluid passageway 52. Alternate sealing means could of course be provided.

Additionally, some form of registration means is preferably provided to assure sealing alignment of any one syringe body fluid conduit with valve body first fluid passageway 52. No such means are shown in the drawing, although any conventional means such as provided in the prior art might be utilized. As one example, a series of a plurality of projections or indentations might be utilized relative to the facial interface of valve body 14 and syringe body 12 which interlockingly engage upon desired alignment. Alternately by way of example only, a corresponding annular groove might be provided about the inner end opening of first fluid passageway 52 in valve body end surface 54 to provide a snap-like engagement of a respective O-ring 68 relative thereto.

In the illustrated and preferred embodiment, syringe body 12 includes outer sidewalls having a flat registration surface associated with each respective barrel. Syringe body 12 is illustrated as having such surfaces 70, 71, 72 and 73 in conjunction with syringe barrels 27, 28, 29 and 30, respectively. Also as evident, first fluid passageway 52 of valve body 14 is oriented to align with the topmost positioned fluid conduit of syringe body 12. The above respective flat surfaces assure the care-giver that the syringe barrel which is being used at any given time to access the patient's catheter is the one having its associated flat surface on top of the catheter access system facing the care-giver.

Substantially rigid sheet 16 is preferably dimensioned and formed of any suitable plastic material capable of supporting valve body 14 and interconnected syringe body 12 as shown and described. "Substantially rigid" in the context of this document is intended to define the supporting characteristics of the sheet in being able to both retainably support the valve body and provide some restriction from longitudinal rotational movement of the valve body when the sheet engages with a patient. The sheet might be constructed to have some flexibility, subject to providing the support and restriction described above.

Sheet 16 includes opposing sides 76 and 78. A pair of saddling projections 80 and 82 integrally formed as part of sheet 16 extend outwardly from side 78 and engage with the outer lateral sides of valve body 14. A pair of recesses 84 and 86 (FIG. 7) are opposingly formed laterally into saddle projections 80 and 82. Such receive corresponding male projections 88 and 90, respectively, which are formed in the outer lateral sides of valve body 14. Sheet 16 is provided with a lateral extent which is greater than the lateral extent of valve body 14. Similarly, rigid sheet 16 is provided with a longitudinal extent which is greater than the combined longitudinal extent of the interconnected valve body 14 and syringe body 12. Further in the preferred and illustrated embodiment, projections 80 and 82 support valve body 14 and rotatably interconnected syringe body 12 solely in a cantilevered manner elevationally above rigid sheet 16. Alternately but less preferred, secondary or other supports might be provided for rotationally supporting syringe body 12 towards its outer longitudinal end 24 for rotation above and relative to sheet 16 in addition to projections 80 and 82.

In positioning or using the above-described system relative to a patient, it is anticipated that sheet 16 would be positioned with its base surface 76 lying atop a patient. Such might further be desirably taped relative to a patient's skin or clipped relative to a patient's gown to restrict movement of sheet 16. In such manners, catheter access system 10 is provided with a restriction means externally associated with valve body 14 to engage between valve body 14 and the patient for restricting longitudinal rotational movement of valve body 14 in space and relative to syringe body 12 and the patient when so engaged. The external restriction means, however, does not inhibit substantial free rotational movement of syringe body 12 in space and relative to valve body 14 and the patient when so engaged. Any rotational movement restriction is rather only provided by the direct interconnection of syringe body 12 relative to valve body 14.

In the illustrated and preferred embodiment described above, the relative engagement of valve body 14 and rigid sheet 16 effectively precludes all longitudinal rotation of valve body 14 relative to syringe body 12 and the patient when so engaged, as a result of recesses 84 and 86 engaging relative to projections 88 and 90. The invention does, however, contemplate engagement of valve body 14 relative to projections 80, 82 without interlocking projection recess engagement, such that longitudinal rotation is restricted somewhat, but may not be precluded. The above-described restriction means is also non-invasive relative to the patient. Other non-invasive restriction means would also of course be conceivably utilized in accordance with the invention for spatially restricting rotation of valve body 14 relative to the patient while otherwise enabling rotation of syringe body 12 for aligning a desired syringe barrel relative to first fluid passageway 52, and ultimate access to patient's catheter.

The above-described catheter access system 10 can be used either to inject medication or other solutions into patients through a CVC or other catheter, or to withdraw a patient's blood through the catheter. In either case, the sequence of steps required to accomplish the desired fluid transfers to or from the patient can be accomplished without the numerous and sequential independent connections previously required. As an example, steps involved in administering a patient medication where heparin removal is first required are described below. Catheter access system 10 is preferably provided in a pre-filled condition by or for the care-giver, ready for immediate connection to a CVC access lumen in a patient, for example. By way of example only, syringe barrel 30 would be pre-filled with a desired medication, syringe barrel 29 pre-filled with a flushing saline, and syringe barrel 28 pre-filled with heparin prior to any access to the catheter. Syringe 27 would not be pre-filled, and utilized as a fluid withdrawal syringe. Also, the internal volume of the various fluid conduits and passageways of the system are preferably initially pre-filled with saline to eliminate air.

With connector 18 of the system connected with the patient's catheter 20 in the orientation shown, plunger assembly 37 is operated to withdraw heparin-containing blood rearward into syringe barrel 27. Syringe barrel 12 is then rotated relative to valve body 14 in a natural and preferred clockwise direction until syringe barrel 30 is aligned with first fluid passageway 52 of valve body 14. Medication therein is then pushed into the catheter and patient. Then, syringe body 12 is rotated clockwise again to position saline syringe barrel 29 on top in alignment with fluid passageway 52. Saline is then pushed in to clear all medication from the catheter into the patient, leaving saline in the catheter. Then clockwise rotation is again conducted until heparin containing barrel 28 is aligned with passageway 52. The plunger of within such barrel is subsequently operated to re-establish the heparin lock within the patient's catheter.

The above system could, of course, be utilized in other manners for administering one or more medications to a patient's catheter or for withdrawing blood for analysis from a catheter, as will be appreciated by medical personnel of skill in the art. By way of example only, the above system could be utilized in emergency situations where a typical sequence of multiple drugs might need to be administered through a patient's catheter apart from any association with a catheter having a heparin lock. In such instances, many or all of the barrels of the syringe apparatus might be provided with medication, as opposed to saline.

In accordance with a methodical aspect of the invention in accessing a catheter which has been evasively inserted into a patient's bloodstream, such comprises the following steps:

providing a multi-barreled syringe body having a base end, an outer end, a longitudinal axis and at least two longitudinally extending barrels, the syringe including an independent fluid conduit associated with each of the two barrels, the two independent fluid conduits extending from their respective barrels toward the syringe body base end at spaced locations, the multi-barreled syringe being provided with an independent plunger associated with each of the two barrels, the multi-barreled syringe body having a valve body operatively connected in fluid tight communication relative to its base end, the valve body and syringe body being mounted for rotation relative to one another about the syringe body longitudinal axis, the valve body including a fluid passageway positioned to align with either selected one of the syringe body fluid conduits when the valve body and syringe body are selectively rotated relative to one another, the valve body including a needle-less mating connector in fluid communication with the fluid passageway for connection with a catheter access line in a patient;

connecting the needle-less mating connector to the external mating connector of the catheter extending from the patient;

restricting the valve body from rotation in space relative to the multi-barreled syringe body and the patient;

rotating the multi-barreled syringe body relative to the valve body and patient about the syringe longitudinal axis while restricting the valve body from rotation in space relative to the multi-barreled syringe body and the patient to align a selected one of the fluid conduits of one of the two barrels with the valve body fluid passageway;

transferring fluid between the one barrel and the catheter through the valve body passageway;

rotating the multi-barreled syringe body relative to the valve body and patient about the syringe longitudinal axis while restricting the valve body from rotation in space relative to the multi-barreled syringe body and the patient to align the other one of the fluid conduits of the other of the two barrels with the valve body fluid passageway; and transferring fluid between the other barrel and the catheter through the valve body passageway.

An alternate construction syringe body 12b is described with reference to FIG. 10. Such is largely similar to syringe body 12 of the above first-described embodiment, but for lack of unitary construction of the syringe body and axle. The FIG. 10 embodiment, rather, comprises a syringe body 13 and separate base member 17 which would be adhered relative to one another. Like numbers from the FIG. 1–7 embodiment are utilized in FIG. 10 where appropriate. Syringe body 13 has a base end 22b, an outer end 24 and longitudinal axis 26. Such further includes longitudinally extending barrels of the first described embodiment which extend between the base and outer ends, with only barrels 27b and 29b being viewable in the FIG. 10 exploded sectional. The barrels differ from those of the FIG. 1–7 embodiment in being essentially open at their respective base end 22b.

Figure 10:
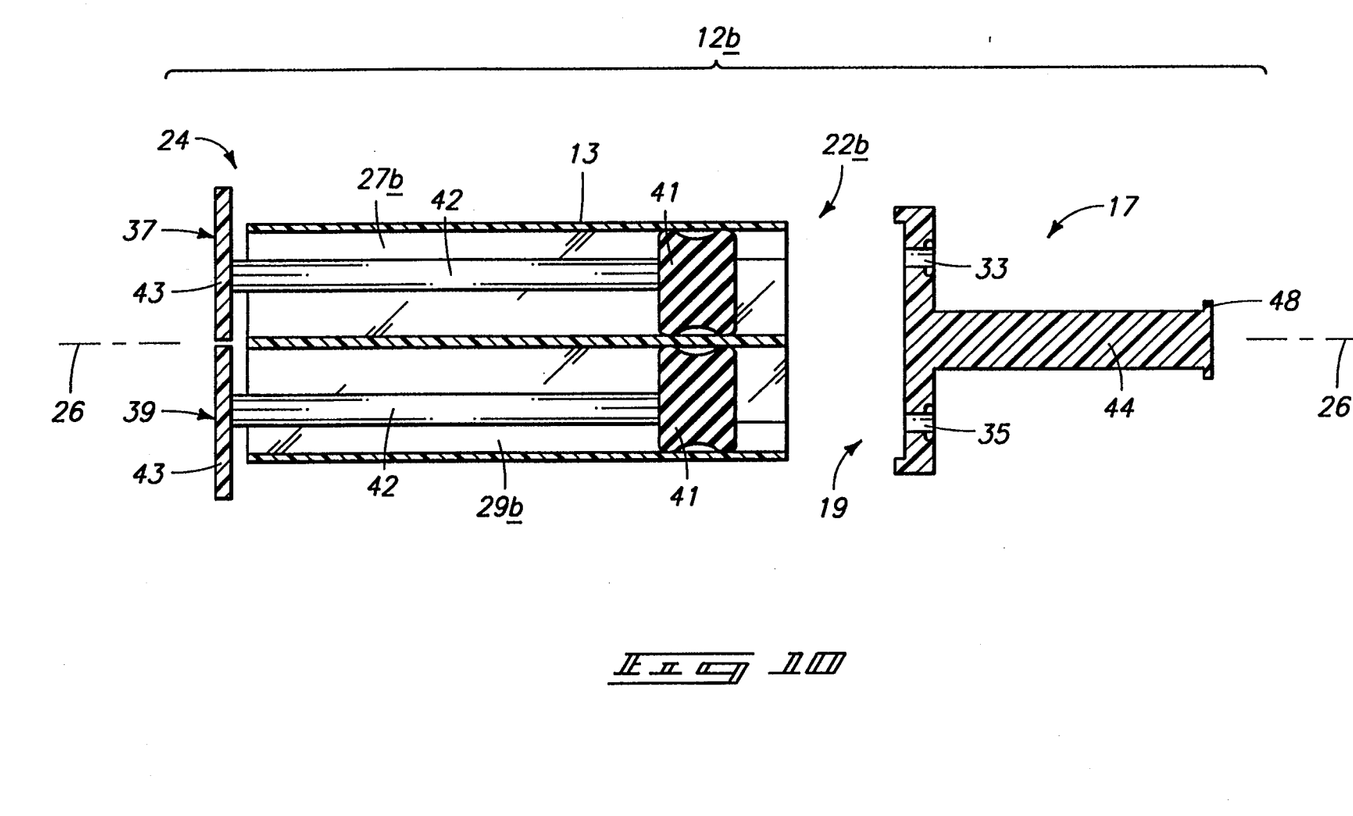
FIG. 10 is a side exploded, sectional view of an alternate syringe body of a catheter access system in accordance with the invention.

Base member 17 includes axle 44, retaining cap 48 and fluid conduits 33, 34, 35 and 36, with only conduits 33 and 35 being viewable in FIG. 10. Base member 17 defines a cavity 19 which is sized to matingly receive syringe body 33 base end 22b therewithin. Such could be retained by adhesive, or by welding or other means to provide an interconnected and well-adhered syringe body unit 12b.

Figure 8:
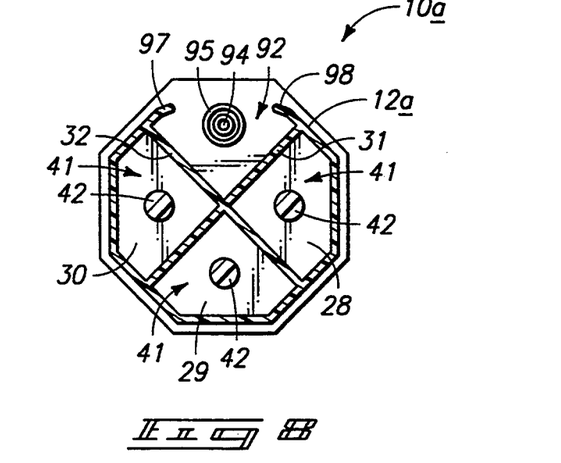
FIG. 8 is a sectional view of an alternate embodiment catheter access system in accordance with the invention as would be positionally taken relative to section line 4—4 in FIG. 3 of the first described embodiment.

Another alternate embodiment catheter access system in accordance with the invention is described with reference to FIGS. 8 and 9, and is generally indicated by reference numeral 10a. Such is similar in construction to the above-described preferred embodiment, such that only differences will be described. Like numerals are utilized where appropriate, with the suffix "a" being utilized with respect to the Figure numerals where construction differences are present.

Figure 9:
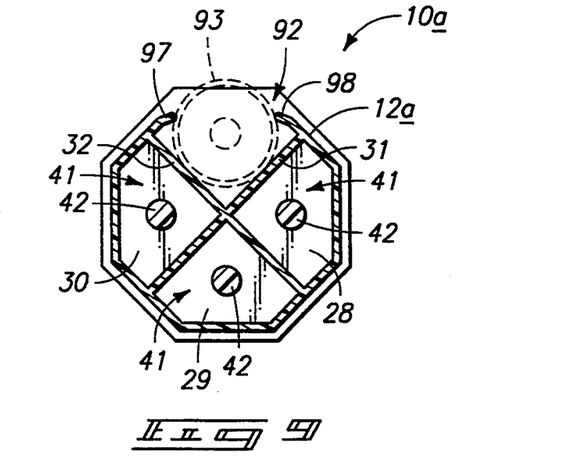
FIG. 9 is a sectional view of the FIG. 8 system positionally taken at the same location, and illustrates operational aspects of the subject alternate embodiment.

Syringe body 12a includes an externally accessible, longitudinally extending cavity 92 which is sized to received a separate longitudinally elongated fluid container, such as by way of example only the illustrated syringe 93 (FIG. 9). Syringe body 12a includes a fluid conduit 94 which extends from cavity 92 toward the syringe body base end, much like fluid conduit 33 of the first described embodiment. Conduit 94 in the illustrated and preferred embodiment terminates in a mating Luer-lok connector 95. Thus, the syringe body includes an externally accessible access port for ultimately separately accessing the catheter. Also as shown, cavity 92 is longitudinally outwardly open along a portion of its length, and more specifically outwardly open along its substantial longitudinal length.

Cavity 92 is further sized to snap-like engage and retain with external sidewalls of elongated syringe container 93. Such is accommodated for by the illustrated longitudinal opposing pairs of extending projections 97, 98, which comprise lateral projections which are positioned to snap engage with the internal sidewalls of the respective container.

Such provides an alternate example regarding how fluid transfer might be facilitated between a patient's catheter and a syringe. Containers other than a syringe 93 might also of course be utilized. For example, the separate container might constitute a vacuum container for blood withdrawal from the catheter. Connector 95 could be reconfigured in a suitable manner to engage relative to such a vacuum container, or other container.

Figure 11:
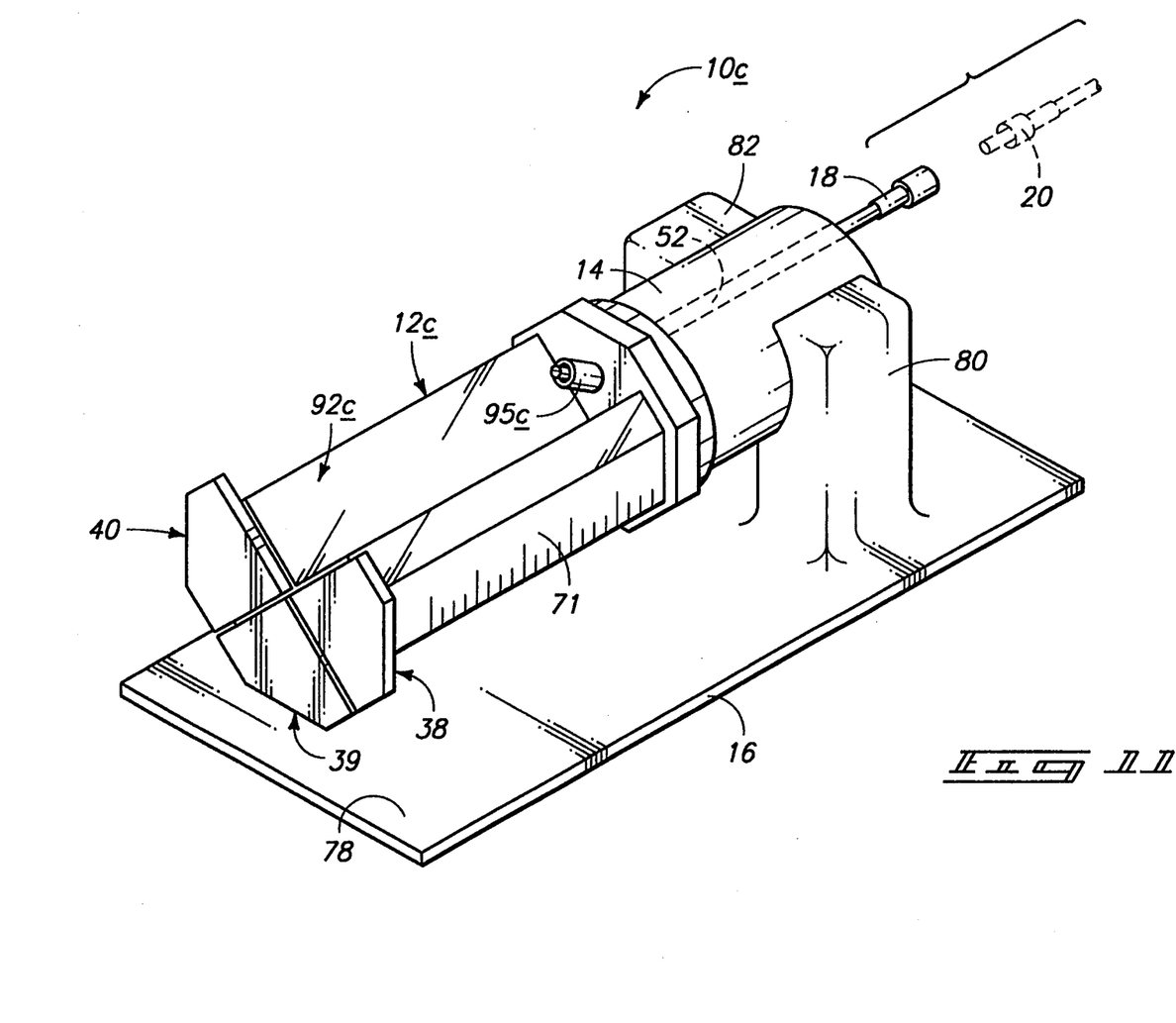
FIG. 11 is an isometric view of yet another alternate catheter access system in accordance with the invention.
Figure 12:
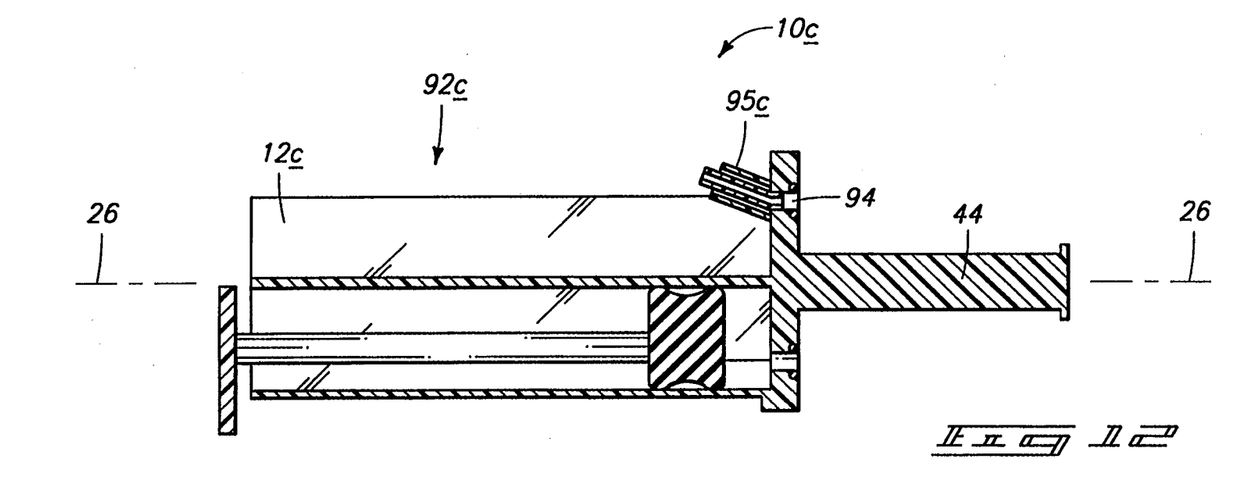
FIG. 12 is a central longitudinal sectional view of the FIG. 11 system.

Yet another alternate embodiment catheter access system in accordance with the invention is described with reference to FIGS. 11, 12, and 13, and is generally indicated by reference numeral 10c. Like numerals from the first two described embodiments are utilized where appropriate. Access system 10c includes a syringe body 12c having a longitudinally elongated cavity 92c which is positioned parallel with syringe body longitudinal axis 26. Third fluid conduit 94 extends to an access port in the form of Luer-lok connector 95c which is angled upwardly or outwardly on the syringe body from longitudinal axis 26 at an angle which is most preferably less than 90° from longitudinal axis 26. Such positions the access port within the confines of cavity 92c and provides minimal fluid flow restriction. One advantage in providing an access port 95c in the manner just described is enabling oversized syringes larger than the confines of cavity 92c to be interconnected with the catheter access system. The illustrated 10c embodiment is further shown void of passageway 56 of the FIGS. 1-7 embodiment. When such a separate passageway is provided, the preferred construction places such on the syringe body as in the FIGS. 8 and 9 and the FIGS. 10-11 embodiments, as opposed to on the valve body as in the FIGS. 1-7 embodiment.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A catheter access system comprising:
    a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;
    an independent plunger associated with each of the two barrels;
    a valve body operatively connected in fluid tight communication relative to the syringe body base end, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient; and
    a non-invasive restriction means externally associated with the valve body to engage between the valve body and the patient for restricting longitudinal rotational movement of the valve body in space relative to the syringe body and patient when so engaged, said external restriction means enabling substantial free rotational movement of the syringe body in space relative to the valve body and the patient when so engaged, the restriction means comprising a substantially rigid sheet engaging the valve body, the longitudinal axis of the syringe body being substantially parallel with the plane of the rigid sheet.

2. A catheter access system comprising:
    a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;
    an independent plunger associated with each of the two barrels:
    a valve body operatively connected in fluid tight communication relative to the syringe body base end, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient; and
    a non-invasive restriction means externally associated with the valve body to engage between the valve body and the patient for restricting longitudinal rotational movement of the valve body in space relative to the syringe body and patient when so engaged said external restriction means enabling substantially free rotational movement of the syringe body in space relative to the valve body and the patient, when so engaged, wherein the restriction means precludes all longitudinal rotation of the valve body relative to the syringe body and patient when so engaged, the restriction means comprising at least one radial projection externally engaging the valve body.

3. A catheter access system comprising:
    a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;

an independent plunger associated with each of the two barrels;

a valve body operatively connected in fluid tight communication relative to the syringe body base end, the valve body and syringe body being mounted for rotation relative to one another about the syringe body longitudinal axis the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient; and a non-invasive restriction means externally associated with the valve body to engage between the valve body and the patient for restricting longitudinal rotational movement of the valve body in space relative to the syringe body and patient when so engaged, said external restriction means enabling substantial free rotational movement of the syringe body in space relative to the valve body and the patient when so engaged, the valve body including outer lateral sides, the restriction means engaging the valve body outer lateral sides to restrict said longitudinal rotational movement.

4. A catheter access system comprising:

a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;

an independent plunger associated with each of the two barrels;

a valve body operatively connected in fluid tight communication relative to the syringe body base end, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway fox connection with a catheter access line in a patient; and a non-invasive restriction means externally associated with the valve body to engage between the valve body and the patient for restricting longitudinal rotational movement of the valve body in space relative to the syringe body and patient when so engaged, said external restriction means enabling substantial free rotational movement of the syringe body in space relative to the valve body and the patient when so engaged, the valve body including outer lateral sides, the restriction means comprising a substantially rigid sheet having a pair of projections extending outwardly from one side thereof, the pair of projections engaging with the valve body outer lateral sides.

5. The catheter access system of claim 4 wherein the projections support the valve body and rotatably interconnected syringe body in a sole cantilevered manner elevationally above the rigid sheet.

6. The catheter access system of claim 4 wherein the rigid sheet has a lateral extent which is greater than a lateral extent of the valve body.

7. The catheter access system of claim 4 wherein the rigid sheet has a longitudinal extent which is greater than a combined longitudinal extent of the valve body and syringe body.

8. The catheter access system of claim 4 wherein the rigid sheet has a lateral extent which is greater than a lateral extent of the valve body, the rigid sheet having a longitudinal extent which is greater than a combined longitudinal extent of the valve body and syringe body.

9. A catheter access system comprising:

a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;

an independent plunger associated with each of the two barrels;

a valve body operatively connected in fluid tight communication relative to the syringe body base end, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient;

a non-invasive restriction means externally associated with the valve body to engage between the valve body and the patient for restricting longitudinal rotational movement of the valve body in space relative to the syringe body and patient when so engaged, said external restriction means enabling substantial free rotational movement of the syringe body in space relative to the valve body and the patient when so engaged; and the valve body further comprising a transfer lumen extending from the first fluid passageway to a location external of the valve body, the transfer lumen terminating in a connection means for connecting a separate syringe to the transfer lumen for transferring fluid between the patient catheter and separate syringe through the valve body first fluid passageway and transfer lumen.

10. A catheter access system comprising:

a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;

an independent plunger associated with each of the two barrels;

a valve body operatively connected in fluid tight communication relative to the syringe body base and, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication, with the first fluid passageway for connection with a catheter access line in a patient;

a non-invasive restriction means externally associated with the valve body to engage between the valve body and the patient for restricting longitudinal rotational movement of the valve body in space relative to the syringe body and patient when so engaged, said external restriction means enabling substantial free rotational movement of the syringe body in space relative to the valve body and the patient when so engaged; and the syringe body including outer sidewalls, the outer sidewalls including a flat registration surface associated with each of the two barrels.

11. A catheter access system comprising:

a syringe body having a base end, an outer end, a longitudinal axis anal at least two longitudinally extending barrels, the syringe body including and independent fluid conduit associated with each of the two barrels, the two independent fluid conduits extending from their respective barrels toward the syringe body base end at spaced locations;

an independent plunger associated with each of the two barrels;

a valve body operatively connected in fluid tight communication relative to the syringe body base end, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient;

a non-invasive restriction means externally associated with the valve body to engage between the valve body and the patient for restricting longitudinal rotational movement of the valve body in space relative to the syringe body and patient when so engaged, said external restriction means enabling substantial free rotational movement of the syringe body in space relative to the valve body and the patient when so engaged;

the syringe body being formed as a unitary body and having an axle integrally formed of the unitary syringe body; the axle having an outer base end, having a diameter and extending outwardly of the base end along the syringe body longitudinal axis;

the valve body having a bore provided therethrough;

the syringe body axle being received through the valve body bore to support the valve body and unitary syringe body relative to one another for rotation about the syringe body longitudinal axis; and the system further comprising:

a retaining cap connected to the outer base end of the unitary syringe body axle, the retaining cap having a radial extent which is greater than the diameter of the axle, the retaining cap bearing against the valve body to rotatably retain the valve body and unitary body together in fluid tight communication.

12. A catheter access system comprising:

a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;

an independent plunger associated with each of the two barrels;

a valve body operatively connected in fluid tight communication relative to the syringe body base end, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient;

a non-invasive restriction means externally associated with the valve body to engage between the valve body and the .patient for restricting longitudinal rotational movement of the valve body in space relative to the syringe body and patient when so engaged, said external restriction means enabling substantial free rotational movement of the syringe body in space relative to the valve body and the patient when so engaged;

the valve body including a second fluid passageway isolated from fluid communication with the first fluid passageway, the second fluid passageway being positioned to align with either selected one of the syringe body fluid conduits when the valve body and syringe body are selectively rotated relative to one another, the valve body including a second outlet in fluid communication with the second fluid passageway.

13. A catheter access system comprising:

a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;

an independent plunger associated with each of the two barrels;

a valve body operatively connected in fluid tight communication relative to the syringe body base end, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient;

a non-invasive restriction means externally associated with the valve body to engage between the valve body and the patient for restricting longitudinal rotational movement of the valve body in space relative to the syringe body and patient when so engaged, said external restriction means enabling substantial free rotational movement of the syringe body in space relative to the valve body and the patient when so engaged;

the syringe body including an externally accessible longitudinally extending cavity sized to receive a separate longitudinally elongated fluid container, the syringe body including a fluid conduit extending from the cavity toward the syringe body base end.

14. A catheter access system comprising:
a unitary syringe body having a base end, an outer end, a longitudinal axis and at least two longitudinally extending barrels; the unitary syringe body including an axle integrally formed of the unitary syringe body; the axle having an outer base end, having a diameter and extending outwardly of the syringe body base end along the syringe body longitudinal axis; the unitary syringe body including an independent fluid conduit associated with each of the two barrels, the two independent fluid conduits extending from their respective barrels toward the syringe body base end at spaced locations;
an independent plunger associated with each of the two barrels;
a valve body having a bore provided therethrough, the syringe body axle being received through the valve body bore to support the valve body and unitary syringe body relative to one another for rotation about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient; and
a retaining cap provided at the outer base end of the unitary syringe body axle, the retaining cap having a radial extent which is greater than the diameter of the axle, the retaining cap bearing against the valve body to rotatably retain the valve body and unitary body together in fluid tight communication.

15. The catheter access system of claim 14 wherein the cap directly contacts against the valve body.

16. The catheter access system of claim 14 wherein the valve body has an outermost base end surface, the cap directly contacting against the valve body outermost base end surface.

17. The catheter access system of claim 14 wherein the valve body further comprises a transfer lumen extending from the first fluid passageway to a location external of the valve body, the transfer lumen terminating in a connection means for connecting a separate syringe to the transfer lumen for transferring fluid between the patient catheter and separate syringe through the valve body first fluid passageway and transfer lumen.

18. The catheter access system of claim 14 wherein the syringe body includes outer sidewalls, the outer sidewalls including a flat registration surface associated with each of the two barrels.

19. The catheter access system of claim 14 wherein the valve body includes a second fluid passageway isolated from fluid communication with the first fluid passageway, the second fluid passageway being positioned to align with either selected one of the syringe body fluid conduits when the valve body and syringe body are selectively rotated relative to one another, the valve body including a second outlet in fluid communication with the second fluid passageway.

20. The catheter access system of claim 14 wherein the syringe body includes an externally accessible longitudinally extending cavity sized to receive a separate longitudinally elongated fluid container, the syringe body including a fluid conduit extending from the cavity toward the syringe body base end.

21. A catheter access system comprising:
a syringe body having a base end, an outer end, a longitudinal axis and at least two longitudinally extending barrels extending between the base and outer ends, the barrels being open at their respective base ends;
a separate base member adhered to the base end of the syringe body, the base member including an outwardly extending axle; the axle having an outer end, having a diameter and extending outwardly along the syringe body longitudinal axis; the base member including an independent fluid conduit aligned with each of the two barrels;
an independent plunger associated with each of the two barrels;
a valve body having a bore provided therethrough, the axle being received through the valve body bore to support the valve body and syringe body with adhered base member relative to one another for rotation about tile syringe body longitudinal axis, the valve body including a first fluid passageway positioned to align with either selected one of the base member fluid conduits when the valve body and syringe body with adhered base member are selectively rotated relative to one another, the valve body including a needle-less mating connector in fluid communication with tile first fluid passageway for connection with a catheter access line in a patient.

22. The catheter access system of claim 21 further comprising a retaining cap provided at the outer end of the axle, the retaining cap having a radial extent which is greater than the diameter of the axle, the retaining cap engaging the valve body to rotatably retain the valve body and syringe body with adhered base member together in fluid tight communication.

23. A catheter access system comprising:
a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;
an independent plunger associated with each of the two barrels;
a valve body operatively connected in fluid tight communication relative to the syringe body base end, the valve body and syringe body being mounted for rotation relative to one another about the syringe body longitudinal axis;
the valve body including a first fluid passageway positioned to align with either selected one of the syringe body fluid conduits when the valve body and syringe body are selectively rotated relative to one another, the valve body including a first outlet comprising a needle-less mating connector in fluid communication with the first fluid passageway for connection with a catheter access line in a patient; and the valve body including a second fluid passageway isolated from fluid communication with the first fluid passageway, the second fluid passageway being positioned to align with either selected one of the syringe body fluid conduits when the valve body and syringe body are selectively rotated relative to one another, the valve body including a second outlet in fluid communication with the second fluid passageway.

24. The catheter access system of claim 23 wherein the first fluid passageway and second fluid passageway are positioned relative to one another to enable only one of the syringe body fluid conduits to be aligned in fluid communication with either of the first or the second fluid passageways at any given point in time.

25. The catheter access system of claim 23 wherein the valve body further comprises a transfer lumen extending from the first fluid passageway to a location external of the valve body, the transfer lumen terminating in a connection means for connecting a separate syringe to the transfer lumen for transferring fluid between the patient catheter and separate syringe through the valve body first passageway and transfer lumen.

26. The catheter access system of claim 23 wherein the syringe body includes outer sidewalls, the outer sidewalls including a flat registration surface associated with each of the two barrels.

27. The catheter access system of claim 23 wherein the syringe body includes an externally accessible longitudinally extending cavity sized to receive a separate longitudinally elongated fluid container, the syringe body including a fluid conduit extending from the cavity toward the syringe body base end.

28. A catheter access system comprising:
a syringe body having a base end, an outer end, a longitudinal axis and at least two longitudinally extending first and second barrels, the syringe body including a first fluid conduit associated with the first barrel and extending toward the syringe body base end, the syringe body including a separate second fluid conduit associated with the second barrel and extending toward the second body base end, an independent plunger associated with each of the first and second barrels; and the syringe body including an externally accessible longitudinally extending cavity sized to receive a separate longitudinally elongated fluid container, the syringe body including an externally accessible access port for the container and a third fluid conduit extending from the access port toward the syringe body base end.

29. The catheter access system of claim 28 wherein the access port is positioned within the cavity.

30. The catheter access system of claim 28 wherein the cavity is sized to snap engage and retain with external sidewalls of a separate longitudinally elongated fluid container.

31. The catheter access system of claim 28 wherein the cavity includes a pair of lateral projections positioned to snap engage and retain with external sidewalls of a separate longitudinally elongated fluid container within the cavity.

32. The catheter access system of claim 28 wherein the cavity is longitudinally outwardly open along a portion of its length.

33. The catheter access system of claim 28 wherein the cavity has a longitudinal length, the cavity being outwardly open along its substantial longitudinal length.

34. The catheter access system of claim 28 wherein, the cavity is longitudinally outwardly open along a portion of its length; and
the cavity includes a pair of lateral projections positioned to snap engage and retain with external sidewalls of a separate longitudinally elongated fluid container within the cavity.

35. The catheter access system of claim 28 wherein, the cavity is outwardly open along its substantial longitudinal length; and
the cavity includes a pair of lateral projections positioned to snap engage and retain with external sidewalls of a separate longitudinally elongated fluid container within the cavity.

36. The catheter access system of claim 28 wherein the syringe body includes outer sidewalls, the outer sidewalls including a flat registration surface associated with each of the two barrels.

37. A catheter access system comprising:
a syringe body having a base end, an outer end, a longitudinal axis and at least two longitudinally extending first and second barrels, the syringe body including a first fluid conduit associated with the first barrel and extending toward the syringe body base end, the syringe body including a separate second fluid conduit associated with the second barrel and extending toward the second body base end, an independent plunger associated with each of the first and second barrels;
a valve body operatively connected in fluid tight communication relative to the syringe body base end, the valve body and syringe body being mounted for rotation relative to one another about the syringe body longitudinal axis; and
the syringe body including an externally accessible access port and a third fluid conduit extending therefrom toward the syringe body base end.

38. The catheter access system of claim 37 wherein the first and second barrels are aligned substantially parallel with the syringe body longitudinal axis, the access port being angled on the syringe body from the longitudinal axis.

39. The catheter access system of claim 37 wherein the first and second barrels are aligned substantially parallel with the syringe body longitudinal axis, the access port being angled on the syringe body at less than 90° from the longitudinal axis.

40. The catheter access system of claim 37 wherein the syringe body includes an externally accessible longitudinally extending cavity, the access port being positioned in the cavity.

41. The catheter access system of claim 37 wherein the first and second barrels are aligned substantially parallel with the syringe body longitudinal axis, the syringe body includes an externally accessible longitudinally extending cavity aligned substantially parallel with the syringe body longitudinal axis, the access port being positioned in the cavity at an angle from the longitudinal axis.

42. The catheter access system of claim 37 wherein the first and second barrels are aligned substantially parallel with the syringe body longitudinal axis, the syringe body includes an externally accessible longitudinally extending cavity aligned substantially parallel with the syringe body longitudinal axis, the access port being positioned in the cavity at an angle less than 90° from the longitudinal axis.

43. A catheter access system comprising:
a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;
an independent plunger associated with each of the two barrels;
a valve body operatively connected in fluid tight communication relative to the syringe body base end, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient; and
a non-invasive restriction means externally associated with the valve body to engage between the valve body and the patient for restricting longitudinal rotational movement of the valve body in space relative to the syringe body and patient when so engaged, said external restriction means enabling substantial free rotational movement of the syringe body in space relative to the valve body and the patient when so engaged;
the valve body having an outer surface, the restriction means engaging the valve body outer surface to restrict said longitudinal rotational movement.

44. A catheter access system comprising:
a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;
an independent plunger associated with each of the two barrels;
a valve body operatively connected in fluid tight communication relative to the syringe body base end, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient; and
a non-invasive restriction means externally associated with the valve body to engage between the valve body and the patient for restricting longitudinal rotational movement of the valve body in space relative to the syringe body and patient when so engaged, said external restriction means enabling substantial free rotational movement of the syringe body in space relative to the valve body and the patient when so engaged, the restriction means being separable from the valve body.

45. A catheter access system comprising:
a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;
an independent plunger associated with each of the two barrels;
a valve body operatively connected in fluid tight communication relative to the syringe body base end, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient; and
a non-invasive restriction means externally associated with the valve body to engage between the valve body and the patient for restricting longitudinal rotational movement of the valve body in space relative to the syringe body and patient when so engaged, said external restriction means enabling substantial free rotational movement of the syringe body in space relative to the valve body and the patient when so engaged, the restriction means being other than integral with the valve body.

46. A catheter access system comprising:
a syringe body having a base end, an outer end, a longitudinal axis and at least two longitudinally extending barrels, the syringe body including an independent fluid conduit associated with each of the two barrels, the two independent fluid conduits extending from their respective barrels toward the syringe body base end at spaced locations;
an independent plunger associated with each of the two barrels;
a valve body operatively connected in fluid tight communication relative to the syringe body base end, the valve body and syringe body being mounted for rotation relative to one another about the syringe body longitudinal axis, the valve body including a first fluid passageway positioned to align with either selected one of the syringe body fluid conduits when the valve body and syringe body are selectively rotated relative to one another, the valve body including a needle-less mating connector in fluid communication with the first fluid passageway for connection with a catheter access line in a patient; and
a non-invasive restriction means externally associated with the valve body to engage between the valve body and the patient for restricting longitudinal rotational movement of the valve body in space relative to the syringe body and patient when so engaged, said external restriction means enabling substantial free rotational movement of the syringe body in space relative to the valve body and the patient when so engaged, the restriction means and valve body comprising a male-female interconnect.

* * * * *